United States Patent
Arai et al.

(10) Patent No.: US 8,747,319 B2
(45) Date of Patent: Jun. 10, 2014

(54) IMAGE DISPLAYING METHOD AND MEDICAL IMAGE DIAGNOSTIC SYSTEM

(75) Inventors: Osamu Arai, Tokyo (JP); Hiroko Satake, Nagoya (JP); Akiko Sawaki, Nagoya (JP)

(73) Assignee: Hitachi Medical Corporation, Tokyo (JP)

(*) Notice: Subject to any disclaimer, the term of this patent is extended or adjusted under 35 U.S.C. 154(b) by 1541 days.

(21) Appl. No.: 12/089,425
(22) PCT Filed: Sep. 22, 2006
(86) PCT No.: PCT/JP2006/318841
§ 371 (c)(1), (2), (4) Date: Jul. 15, 2009
(87) PCT Pub. No.: WO2007/043310
PCT Pub. Date: Apr. 19, 2007

(65) Prior Publication Data
US 2009/0306504 A1 Dec. 10, 2009

(30) Foreign Application Priority Data
Oct. 7, 2005 (JP) ................ 2005-295108

(51) Int. Cl.
A61B 8/14 (2006.01)
A61B 8/08 (2006.01)
A61B 6/00 (2006.01)
G06T 19/00 (2011.01)
G06T 15/08 (2011.01)
A61B 5/055 (2006.01)
G01S 7/52 (2006.01)
G01S 15/89 (2006.01)

(52) U.S. Cl.
CPC . *A61B 8/483* (2013.01); *A61B 8/14* (2013.01); *A61B 8/523* (2013.01); *A61B 6/466* (2013.01); *G06T 19/00* (2013.01); *G06T 15/08* (2013.01); *G06T 2219/008* (2013.01); *A61B 5/055* (2013.01); *G01S 7/52074* (2013.01); *G01S 15/8993* (2013.01)
USPC ........... 600/443; 600/437; 345/419; 345/424; 382/128

(58) Field of Classification Search
None
See application file for complete search history.

(56) References Cited

U.S. PATENT DOCUMENTS 5,329,929 A * 7/1994 Sato et al. .......... 600/441
5,720,291 A * 2/1998 Schwartz .......... 600/456

(Continued)

FOREIGN PATENT DOCUMENTS

EP 1 308 903 5/2003
FR 2 863 085 6/2005

(Continued)

OTHER PUBLICATIONS

Takao Iwasaki, "Real-time Virtual Sonography (RVS)", Eizo Joho Medical, Nov. 1, 2004, 2004 Nen 11 Gatsugo Furoku, pp. 6 to 9.

(Continued)

*Primary Examiner* — Long V. Le
*Assistant Examiner* — Bradley Impink
(74) *Attorney, Agent, or Firm* — Antonelli, Terry, Stout & Kraus, LLP.

(57) ABSTRACT

The image display method comprises a three-dimensional image creating step that creates a three-dimensional image based on volume data; a cutting plane setting step that sets a cutting plane that cuts the three-dimensional image at an arbitrary position; and a positional relationship display image creating step that creates a positional relationship display image representing the mutual positional relationship between the three-dimensional image and the cutting plane, in which the opacity of the cutting plane in the positional relationship display image is adjusted so that a portion of the three-dimensional image that is hidden by the cutting plane is visually recognizable through the cutting plane in the positional relationship display image.

21 Claims, 11 Drawing Sheets

(56) References Cited

U.S. PATENT DOCUMENTS

| | | | |
|---|---|---|---|
| 5,879,302 A * | 3/1999 | Hashimoto et al. | 600/441 |
| 6,254,540 B1 | 7/2001 | Kikuchi et al. | |
| 6,283,918 B1 * | 9/2001 | Kanda et al. | 600/441 |
| 6,480,732 B1 * | 11/2002 | Tanaka et al. | 600/425 |
| 6,511,426 B1 * | 1/2003 | Hossack et al. | 600/437 |
| 7,215,325 B2 | 5/2007 | Kim | |
| 7,604,595 B2 * | 10/2009 | Steen et al. | 600/437 |
| 2003/0097068 A1 * | 5/2003 | Hossack et al. | 600/443 |
| 2003/0125624 A1 * | 7/2003 | Shiki | 600/443 |
| 2005/0033160 A1 * | 2/2005 | Yamagata et al. | 600/425 |

FOREIGN PATENT DOCUMENTS

| | | |
|---|---|---|
| JP | 2000-000238 | 1/2000 |
| JP | 2000-245487 | 9/2000 |
| JP | 2001-84409 | 3/2001 |
| JP | 2001-224597 | 8/2001 |
| JP | 2003-180697 | 7/2003 |
| WO | WO 01/97174 | 12/2001 |

OTHER PUBLICATIONS

Atherton, P.R.: "A method of Interactive Visualization of CAD Surface Models on a color Video Display", Computer Graphics, ACM, US vol. 15, No. 3, Aug. 1, 1981, pp. 279-287, whole document.

Delabays A, et al, "Transthoracic real-time three-dimensional echocardiography using a fan-like scanning approach for data acquisition: methods, strengths, problems, and initial clinical experience." Echocardiography (Mount Kisco, NY) Jan 1. 1995, vol. 12, No. 1, pp. 49-59, whole document.

* cited by examiner

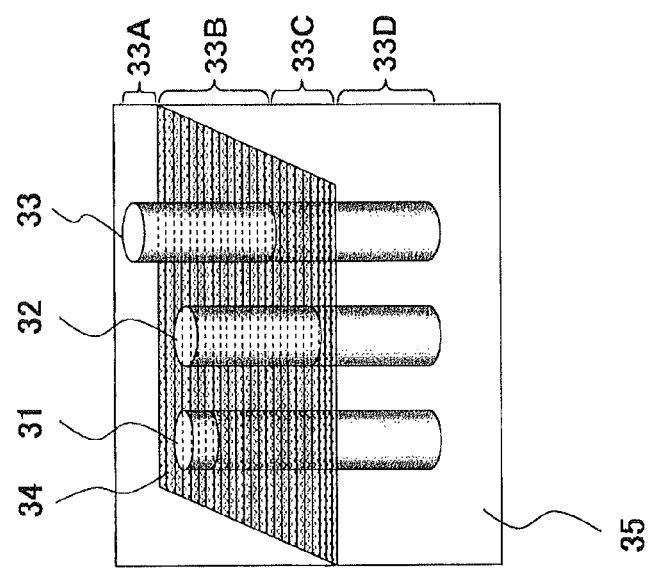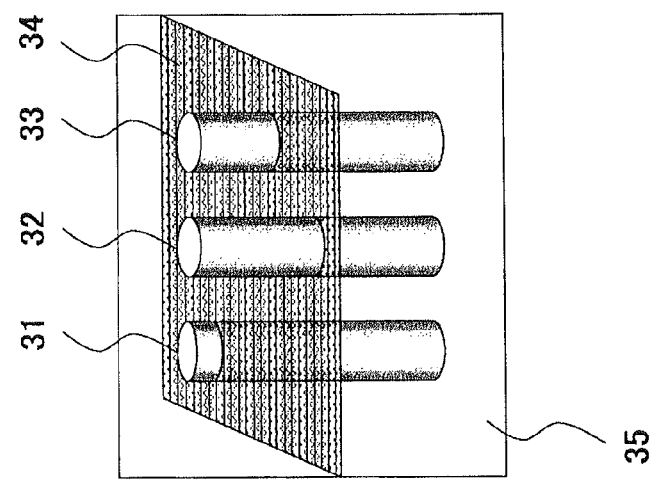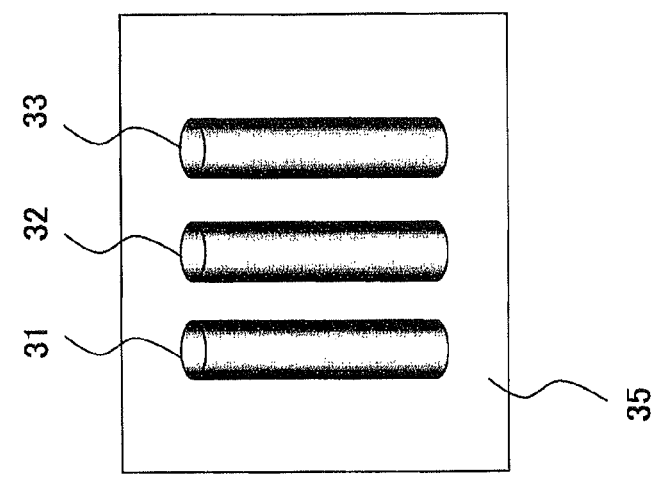

</br>

IMAGE DISPLAYING METHOD AND MEDICAL IMAGE DIAGNOSTIC SYSTEM

TECHNICAL FIELD

The present invention relates to an image displaying method which three-dimensionally displays an image obtained from a subject, and a medical image diagnostic system. The present application claims the benefit of priority under the Paris Convention based on Japanese Patent Application No. 2005-295108 according to Japanese Patent Law, and claims the benefit of the Japanese Patent Application No. 2005-295108 which is incorporated herein by reference.

BACKGROUND ART

Maximum Intensity Projection (MIP) is a method for displaying a three-dimensional image with a medical image diagnostic apparatus. In the MIP method, a line of vision is considered that corresponds to each pixel constituting an image (MIP image) the operator is attempting to obtain as a result, and by taking the maximum values among luminances of pixels present on the line of vision in volume data of a target object as the luminance values of pixels corresponding to the MIP image, an MIP image which three-dimensionally displays image data obtained from the target object is obtained.

DISCLOSURE OF THE INVENTION

Because the information for depth in the line of vision direction is lost in an MIP image, an MIP image is a planar image. Accordingly, since an operator cannot recognize the depth relationship between blood vessels from a two-dimensionally displayed MIP image, the operator must view the MIP image in combination with a visualized image from a line of vision at another angle in order to recognize the depth relationship between blood vessels. Therefore, the efficiency and operability is poor. Thus, a method may be considered in which depth information is added to a three-dimensional image and displayed.

For example, Japanese Patent Application Laid-Open No. 2000-245487 discloses technology that displays an image obtained by synthesizing a projection image of a three-dimensional image produced by volume rendering and an image of a cross section displaying voxel values at cross-sectional positions that are set inside the volume. However, Japanese Patent Application Laid-Open No. 2000-245487 contains no disclosure or suggestion regarding a specific method for synthesizing the images.

An object of the present invention is to create and display a three-dimensional image that is assigned with depth information.

In order to solve the above described problem, the present invention relates to an image display method comprising: a three-dimensional image creating step of creating a three-dimensional image based on volume data; a cutting plane setting step of setting a cutting plane that cuts the three-dimensional image at an arbitrary position; and a positional relationship display image creating step of creating a positional relationship display image which represents a mutual positional relationship between the three-dimensional image and the cutting plane, a positional relationship display image in which an opacity in the positional relationship display image of the cutting plane is adjusted so that a portion of the three-dimensional image that is hidden by the cutting plane is visually recognizable through the cutting plane in the positional relationship display image.

Preferably, in the positional relationship display image creating step, the opacity of at least one of the three-dimensional image and the cutting plane in the positional relationship display image is adjusted so that a portion in which the three-dimensional image and the cutting plane overlap and a portion in which the three-dimensional image and the cutting plane do not overlap are displayed differently in the positional relationship display image.

Further preferably, the image display method further includes a body surface image creating step of creating a body surface image of an object to be examined based on the volume data, and in the positional relationship display image creating step, the positional relationship display image is created so as to represent the mutual positional relationship between the three-dimensional image, the cutting plane, and the body surface image.

Further, in order to solve the above described problem, the present invention relates to a medical image diagnostic system comprising: a volume data storage device which stores volume data relating to an object to be examined; a three-dimensional image creating device which creates a three-dimensional image based on the volume data; a cutting plane setting device which sets a cutting plane which cuts the three-dimensional image at an arbitrary position; and a positional relationship display image creating device which creates a positional relationship display image which represents a mutual positional relationship between the three-dimensional image and the cutting plane, the positional relationship display image in which an opacity in the positional relationship display image of the cutting plane is adjusted so that a portion of the three-dimensional image that is hidden by the cutting plane is visually recognizable through the cutting plane in the positional relationship display image.

Preferably, the medical image diagnostic system further comprises: a probe which transmits and receives ultrasonic waves to and from the object to be examined; an ultrasonic wave transmitting and receiving device which supplies a driving signal to the probe and also processes a reception signal that is output from the probe to output reception data; an ultrasonic image creating device which reconstructs an ultrasonic image based on the reception data that is output from the ultrasonic wave transmitting and receiving device; and a display device which displays at least one of the positional relationship display image and the ultrasonic image.

Further preferably, the medical image diagnostic system further comprises a reference image creating device which creates a reference image of the same cross section as the ultrasonic image based on the volume data and the positional information of the probe, and the display device displays the reference image.

According to the present invention, depth can be expressed in a three-dimensional image including, for example, an MIP image.

BRIEF DESCRIPTION OF THE DRAWINGS

FIGS. 3A, 3B, and 3C are views for describing display modes of the first embodiment;

DESCRIPTION OF SYMBOLS

10 . . . medical image diagnostic apparatus, 11 . . . volume data storage unit, 12 . . . MIP image creating unit, 13 . . . cutting plane creating unit, 14 . . . positional relationship display image creating unit, 15 . . . display unit, 16 . . . control unit, 17 . . . operation unit, 21 . . . viewpoint, 22 . . . line of vision, 23 . . . volume data, 24 . . . plane of projection, 25 . . . data string of voxel data, 26 . . . voxel with maximum luminance value, 27 . . . pixels of plane of projection, 31 . . . MIP image of blood vessel, 32 . . . MIP image of blood vessel, 33 . . . MIP image of blood vessel, 34 . . . cutting plane, 35 . . . MIP image, 36 . . . SR image representing body surface of an object to be examined, 50 . . . ultrasonic probe, 51 . . . ultrasonic wave transmitting and receiving unit, 52 . . . ultrasonic image creating unit, 53 . . . magnetic sensor, 54 . . . ultrasonic tomographic plane coordinates calculation unit, 55 . . . reference image creating unit, 56 . . . display unit, 57 . . . ultrasonic diagnostic apparatus, 58 . . . three-dimensional image creating unit, 59 . . . positional data calculating unit, 60 . . . positional relationship display image, 61 . . . display area of ultrasonic image, 62 . . . display area of reference image, 63 . . . ultrasonic image, 64 . . . reference image, 65 . . . cross-sectional image of blood vessel, 66 . . . cross-sectional image of blood vessel, 67 . . . cross-sectional image of blood vessel, D . . . depth of ultrasonic image, F . . . field of view of ultrasonic image, PR . . . probe radius

BEST MODE FOR CARRYING OUT THE INVENTION

Figure 1:
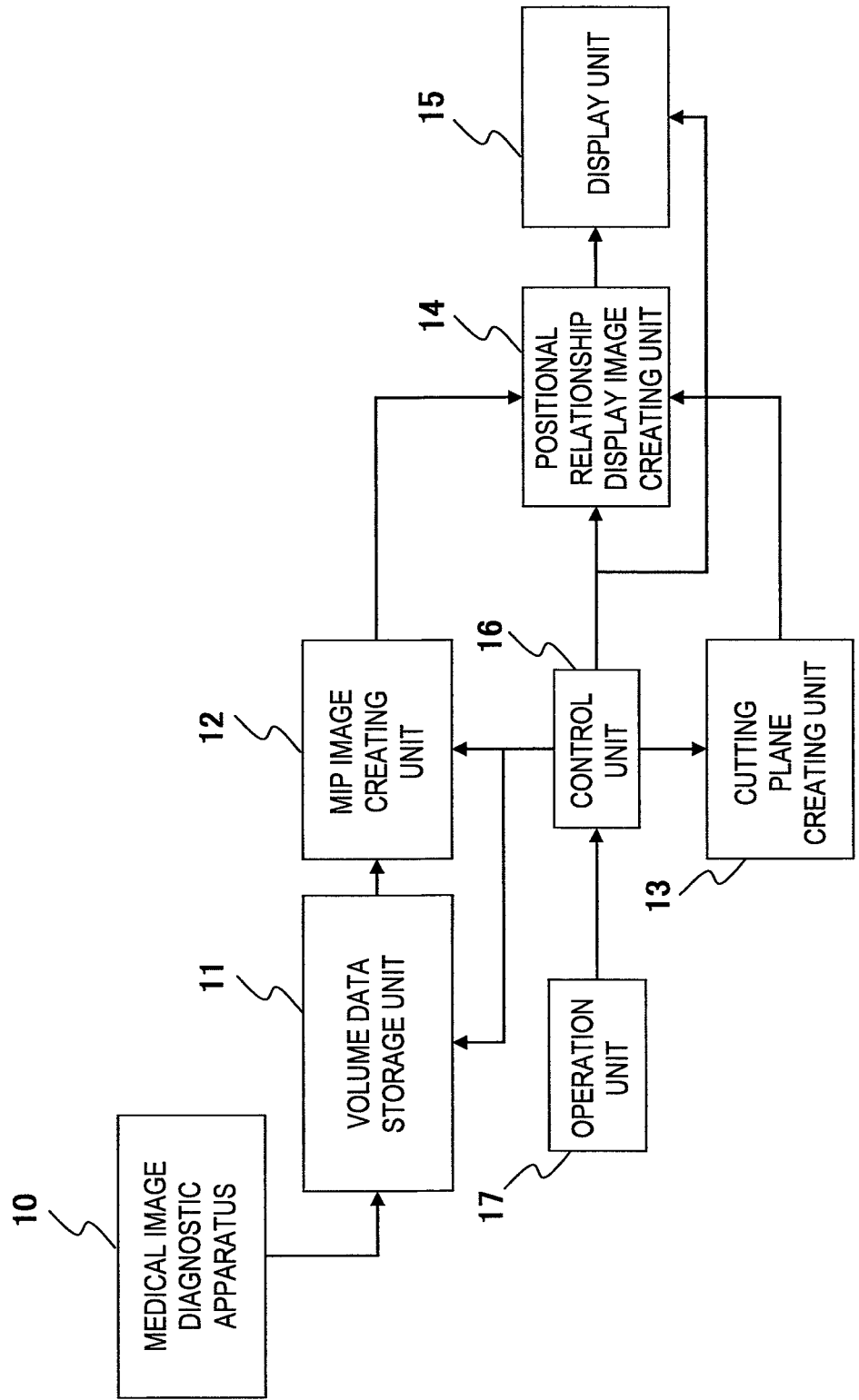
FIG. 1 is a configuration diagram that illustrates a first embodiment of the present invention.

The first embodiment of the present invention will now be described using FIGS. 1 to 5. FIG. 1 is a system configuration diagram of a medical image diagnostic system according to the first embodiment. This medical image diagnostic system includes: a medical image diagnostic apparatus 10 which acquires three-dimensional volume data from an object to be examined; a volume data storage unit 11 which stores volume data acquired by the medical image diagnostic apparatus 10; an MIP image creating unit 12 which creates an MIP image based on volume data stored by the volume data storage unit 11; a cutting plane creating unit 13 which creates a cutting plane in a three-dimensional space; a positional relationship display image creating unit 14 which creates a positional relationship display image representing a mutual positional relationship between an MIP image and a cutting plane; a display unit 15 which displays a positional relationship display image created by the positional relationship display image creating unit 14; a control unit 16 comprising a CPU (Central Processing Unit), and which controls each of the above-described components; and an operation unit 17 comprising a mouse, a trackball, a keyboard or the like, and which supplies an instruction from an operator to the control unit 16.

The medical image diagnostic apparatus 10 is, for example, any of a CT (Computed Tomography) image diagnostic apparatus, an MR (Magnetic Resonance) image diagnostic apparatus, and an ultrasonic image diagnostic apparatus, and is an image diagnostic apparatus which acquires three-dimensional volume data of an object to be examined. For example, volume data acquired with a CT image diagnostic apparatus is data obtained from CT values that are calculated based on X-ray absorption values at certain locations of an object to be examined corresponding to the volume. Further, volume data obtained with an MR image diagnostic apparatus is data obtained from measurement values of proton density and the like at certain locations of an object to be examined corresponding to the volume.

The volume data storage unit 11 stores volume data acquired by the medical image diagnostic apparatus 10 in a memory or the like together with the three-dimensional position coordinates thereof, and can also store multiple kinds of volume data acquired by various image diagnostic apparatuses.

The MIP image creating unit 12 creates an MIP image using an MIP method based on volume data stored in the volume data storage unit 11. According to the MIP method, with respect to volume data, a plane of projection that is a two-dimensional structure is disposed in a three-dimensional space with a dispositional relationship corresponding to the plane of projection and a viewpoint specified by an operator. The values of data having the largest values among given data on a projection line are determined as the projection values for each pixel on the plane of projection of the volume data. By taking projection values determined in this manner as the values for each pixel, an MIP image based on the plurality of pixels is displayed.

Figure 2:
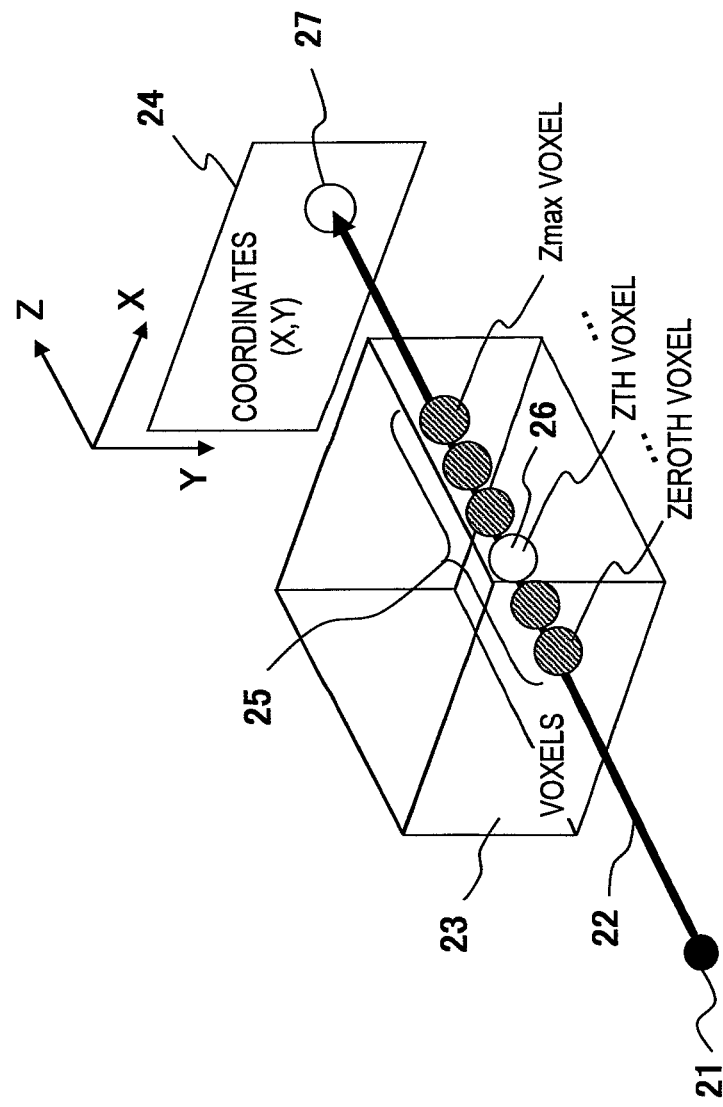
FIG. 2 is a view for describing an MIP method.

This MIP method will now be described in detail using FIG. 2. Volume data 23 is stored together with the three-dimensional coordinates thereof in the volume data storage unit 11. For a line of vision 22 that passes through the volume data 23 from a viewpoint 21 of the operator and reaches a pixel 27 (coordinates (X,Y)) on the plane of projection 24, the luminance of a voxel 26 having a maximum luminance among a volume data string 25 on the line of vision 22 is taken as the luminance of the pixel 27 on the plane of projection 24 to be displayed on the display unit 15. In this case, for the purposes of description, the plane of projection 24 is referred to as the XY plane and the line of vision direction is referred to as the Z-axis direction.

The line of vision 22 from the operator's viewpoint 21 passes through the volume data 23, and the line of vision 22 and the plane of projection 24 intersect at position (X,Y). The volume data 23 on the line of vision 22 is the data string of the voxel data 25 from the voxel at the zeroth position to the voxel at the Zmax position. A comparison of luminance values is performed from the viewpoint 21 with respect to the data string 25 on the line of vision 22. More specifically, the luminance value of the voxel data for the zeroth position is compared with the luminance value of the voxel data for the $1^{st}$ position adjoining thereto, and the higher luminance value is taken to be the maximum luminance value. Subsequently, the thus-determined maximum luminance value is compared with the luminance value of the voxel data for the $2^{nd}$ position, and the higher luminance value is taken to be the maximum luminance value. This comparison operation is repeated until the voxel data for the voxel at the Zmax position.

For example, when the luminance value of the $n^{th}$ voxel data is expressed by a general formula as luminance value $B_n$ (n is an integer, and $0 \leq n \leq Zmax-1$), if $B_n \geq B_{(n+1)}$, then $B_n$ is taken as the maximum luminance value, and if $B_n < B_{(n+1)}$, then $B_{(n+1)}$ is taken as the new maximum luminance value. Thus, the maximum luminance value determined after performing operations to compare luminance values for values from n=0 to n=Zmax−1 is taken as the luminance value of the pixel 27 on the plane of projection 24. For example, when the luminance value of the voxel 26 at the Zth position is the maximum luminance value, the luminance value of the voxel 26 is taken as the luminance value of position (XY) on the plane of projection 24. In this manner, the MIP image creating unit 12 determines maximum luminance values corresponding to positions (XY) for the entire plane of projection 24 to create an MIP image that is constituted by the maximum luminance value of each point.

The cutting plane creating unit 13 creates a cutting plane in an XYZ three-dimensional space that takes the plane of projection as the XY plane and the line of vision direction as the Z axis. For example, when the cutting plane passes a point $(X_0, Y_0, Z_0)$ and a rotational component R of the cutting plane is:

[Formula 1]

$$R = \begin{bmatrix} m11 & m12 & m13 \\ m21 & m22 & m23 \\ m31 & m32 & m33 \end{bmatrix} \quad (1)$$

coordinates (X, Y, Z) within a three-dimensional space at a point $(X_{2D}, Y_{2D})$ on the cutting plane coordinate system are:

[Formula 2]

$$\begin{bmatrix} X \\ Y \\ Z \\ 1 \end{bmatrix} = \begin{bmatrix} m11 & m12 & m13 & X_0 \\ m21 & m22 & m23 & Y_0 \\ m31 & m32 & m33 & Z_0 \\ 0 & 0 & 0 & 1 \end{bmatrix} \cdot \begin{bmatrix} X_{2D} \\ X_{2D} \\ 0 \\ 1 \end{bmatrix} \quad (2)$$

The operator can change an angle and a position inside the three-dimensional space of the cutting plane via the operation unit 17. For example, the operator can change the point $(X_0, Y_0, Z_0)$ to move the three-dimensional position of the cutting plane by clicking with a mouse on a center part of a cutting plane displayed on the screen of the display unit 15 to specify the cutting plane and operating the trackball. Further, by clicking on an end of the cutting plane displayed on the screen of the display unit 15 with a mouse to specify the cutting plane and operating the trackball, the operator can change the rotational component R to cause the cutting plane to rotate by taking the center of the cutting plane as a pivot. In this connection, the shape of the cutting plane is not limited to a square shape, and may be a round shape or a fan shape, or may be a convex shape that corresponds to the depth and field of view of the ultrasonic image.

Based on the MIP image created with the MIP image creating unit 12 and the cutting plane created with the cutting plane creating unit 13, the positional relationship display image creating unit 14 creates a positional relationship display image that represents the mutual positional relationship between the MIP image and the cutting plane. At this time, in the positional relationship display image, the cutting plane and the MIP image are represented by mutually different hues. For example, the cutting plane is green and the MIP image is black and white or red.

The technique for creating a positional relationship display image based on the MIP image and the cutting plane will now be described in detail. The Z coordinate value of a voxel that is determined to have the maximum luminance value on the line of vision 22 corresponding to the position (XY) on the MIP image created by the MIP image creating unit 12 is taken as $Z_M$. The Z coordinate value of the position (XY) on the cutting plane created by the cutting plane creating unit 13 is taken as $Z_S$. In this connection, in this case the Z coordinate value for the position nearest the viewpoint 21 among the volume data 23 on the line of vision 22 is taken as zero.

The positional relationship display image creating unit 14 compares $Z_M$ and $Z_S$ to determine which among the MIP image and the cutting plane is nearer to the viewpoint 21, and executes hidden surface removal processing. When it is determined that $Z_M < Z_S$ indicating that the MIP image is nearer to the viewpoint 21 than the cutting plane at the position (XY) on the positional relationship display image, the luminance value of the MIP image is employed for the luminance value on the positional relationship display image. Alternatively, a configuration may be adopted in which, by setting the opacity for the MIP image and the cutting plane, respectively, in advance, and performing a process of weighted addition on luminance values in the Z order in a manner whereby the weighting of a coefficient increases as the opacity increases, the MIP image on the front side is displayed translucently and the cutting plane on the depth side is displayed through the MIP image. As a result, in the positional relationship display image, the MIP image appears to be further on the front side than the cutting plane. Further, when it is determined that $Z_M > Z_S$ indicating that the MIP image is farther from the viewpoint 21 than the cutting plane, the luminance value of the cutting plane is employed for the luminance value of the positional relationship display image. Alternatively, a configuration may be adopted in which, by performing a process of weighted addition on luminance values in the Z order in a manner whereby the weighting of a coefficient increases as the opacity increases, the cutting plane on the front side is displayed translucently and the MIP image on the depth side is displayed through the cutting plane. As a result, in the positional relationship display image, the cutting plane appears to be further on the front side than the MIP image. When it is determined that $Z_M = Z_S$, the positional relationship display image creating unit 14 sets the luminance value at the position (XY) on the display image to, for example, blue. As a result, in the positional relationship display image, the boundary line between the cutting plane and the MIP image is represented by a blue color to clearly display the boundary line. In this case, a configuration is adopted so that the opacity of a cutting plane and the opacity of an MIP image can be respectively set to arbitrary values by the operator.

The display unit 15 displays a positional relationship display image that represents the mutual positional relationship between a cutting plane and an MIP image that is created by the positional relationship display image creating unit 14. By displaying the cutting plane in addition to the MIP image in this manner, depth information can be assigned to the MIP image and displayed so that, for example, the depth relationship of blood vessels can be represented in an MIP image displaying the blood vessels to enable the depth relationship to be recognized by the operator.

FIGS. 3A, 3B, and 3C are views that describe modes in which a positional relationship display image representing the mutual positional relationship between an MIP image and a cutting plane are displayed on the display unit 15. FIG. 3A is a view showing an MIP image 35 in which a cutting plane 34 is not set. FIG. 3B is a view showing a positional relationship display image that is created based on the cutting plane 34 and the MIP image 35 in a case in which the cutting plane 34 is set. FIG. 3C is a view showing another example of a positional relationship display image.

As shown in FIG. 3A, in the MIP image 35 in which the cutting plane 34 is not set, the depth relationship between blood vessels 31, 32, and 33 is not represented, and therefore an operator cannot recognize which blood vessel is located at the front side and which blood vessel is located on the inner side. In contrast, as shown in FIG. 3B, with a positional relationship display image in which the cutting plane 34 is set in the MIP image 35 and which is created based on the cutting plane 34 and the MIP image 35, based on the positional relationship between each of the blood vessels 31, 32, and 33 and the cutting plane 34 the operator can recognize that the blood vessel 32 is located furthest on the front side, the blood vessel 31 is located furthest on the inner side, and the blood vessel 33 is located between the blood vessel 32 and the blood vessel 31, to thereby recognize the depth relationship between the blood vessels 31, 32, and 33.

FIG. 3C is a view showing an example of a positional relationship display image displaying the positional relationship between the cutting plane 34 and the MIP image 35 by a different method from FIG. 3B. In FIG. 3C, for example, focusing on the blood vessel 33, the display of portions indicated by reference characters 33B and 33C in the figure that are portions at which the blood vessel 33 and the cutting plane 34 overlap, and the display of portions indicated by reference characters 33A and 33D in the figure that are portions at which the blood vessel 33 and the cutting plane 34 do not overlap are displayed differently to each other. That is, the display of the portion 33B at which the blood vessel 33 is on the front side and overlaps with the cutting plane 34 that is on the rear side and the display of the portion 33A (or 33D) at which the blood vessel 33 and the cutting plane 34 do not overlap are displayed differently to each other. Alternatively, the display of the portion 33C at which the cutting plane 34 is on the front side and overlaps with the blood vessel 33 that is on the rear side and the display of the portion 33D (or 33A) at which the blood vessel 33 and the cutting plane 34 do not overlap are displayed differently to each other. As a method for varying the displays, for example, both displays are synthesized and displayed so that the front side is more distinctly recognizable visually than the rear side. Conversely, both displays are synthesized and displayed so that the rear side is more obscure visually than the front side.

Further, for the blood vessel 33, in relation to the portion on the upper side as divided by the cutting plane 34, the display of the portion 33B in which the blood vessel 33 and the cutting plane 34 overlap and the display of the portion 33A in which the blood vessel 33 and the cutting plane 34 do not overlap are displayed differently to each other. Furthermore, for the blood vessel 33, in relation to the portion on the lower side as divided by the cutting plane 34, the display of the portion 33C in which the blood vessel 33 and the cutting plane 34 overlap and the display of the portion 33D in which the blood vessel 33 and the cutting plane 34 do not overlap are displayed differently to each other. The method for varying the displays is as described above.

Also, the display of the portion 33B in which the blood vessel 33 is on the front side and overlaps with the cutting plane 34 on the rear side and the display of the portion 33C in which cutting plane 34 is on the front side and overlaps with the blood vessel 33 on the rear side are displayed differently to each other. The method for varying the displays is as described above.

The control unit 16 issues a setting command for the size of the volume data 23 to the volume data storage unit 11, and can change the size of the volume data 23. For example, by setting the size of the volume data 23 so as to keep data for a region of interest or blood vessels and delete data for bones or the body surface among the volume data 23, a setting can be made so as to display only blood vessels or a region of interest. The control unit 16 also issues a setting command to the MIP image creating unit 12 with respect to the position of the viewpoint 21, the angle of the line of vision 22, and the size of the plane of projection 24. In accordance with the command from the control unit 16, the MIP image creating unit 12 arbitrarily sets the viewpoint 21 inside the three-dimensional space, sets the angle of the line of vision 22 by taking the viewpoint 21 as the center, and sets the size of the plane of projection 24. Further, the control unit 16 issues a setting command to the cutting plane creating unit 13 with respect to the size, shape, position, and angle of the cutting plane. In accordance with the instruction of the control unit 16, the cutting plane creating unit 13 changes the shape of the cutting plane into a quadrangular shape, a round shape, a fan shape, or a convex shape corresponding to an ultrasonic image or the like, sets the size of the cutting plane, and sets the position and angle inside the three-dimensional space of the cutting plane.

The control unit 16 also issues a display mode setting command to the positional relationship display image creating unit 14 and the display unit 15. In accordance with the command from the control unit 16, the positional relationship display image creating unit 14 and the display unit 15 set the display area size and image disposition of the MIP image configured by the MIP image creating unit 12 and the cutting plane configured by the cutting plane creating unit 13 based on volume data relating to the object to be examined. Further, in accordance with the command from the control unit 16, as necessary the positional relationship display image creating unit 14 and the display unit 15 additionally set the size and image disposition of a display area that shows circular cross-sectional slices of the object to be examined, a display area that shows short-axis cross sections of the object, and a display area showing cross sections along the horizontal axis of the object.

The operation unit 17 comprises a keyboard or the like and a pointing device such as a mouse or a trackball. The operator inputs instructions for numerical values or a display range or the like necessary for the various settings described above of the control unit 16 through the operation unit 17. The operation unit 17 includes a magnetic sensor described later, and can also set a position and an angle of a cutting plane according to the position of the magnetic sensor.

Figure 4:
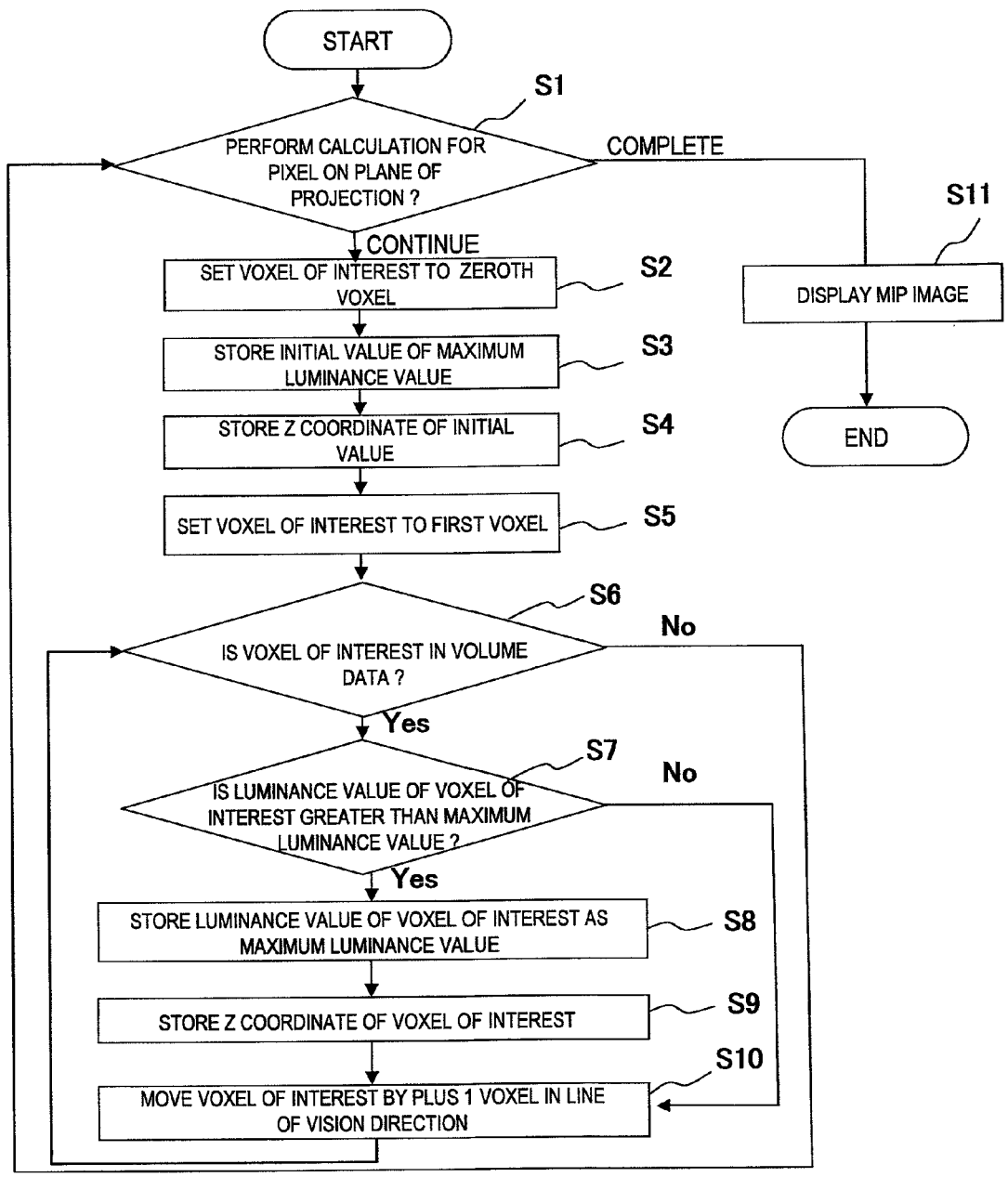
FIG. 4 is a view that illustrates operation procedures of the MIP method.

Next, the operation procedures of the MIP image creating unit 12 are described using FIG. 4.

First, the MIP image creating unit 12 decides whether or not to perform a calculation for pixels on the plane of projection 24 (step S1). When the MIP image creating unit 12 decides to perform a calculation at step S1, it sets the voxel of interest as the zeroth voxel. That is, the MIP image creating unit 12 sets the data of the volume data 23 that is nearest the viewpoint 21 among the volume data 23 on the line of vision 22 as the voxel data of the voxel of interest (step S2). The MIP image creating unit 12 stores the luminance value of the zeroth voxel that is set as the voxel of interest as the initial value for the maximum luminance value (step S3). Subsequently, the MIP image creating unit 12 takes the Z coordinate of the zeroth voxel as being, for example, 0 as the initial value of the Z coordinate, and stores that value together with the initial value for the maximum luminance value (step S4).

Next, the MIP image creating unit 12 sets the voxel of interest as the first voxel that is adjacent to the zeroth voxel. More specifically, the MIP image creating unit 12 moves the voxel of interest towards the rear side by the amount of one voxel from the zeroth voxel in the line of vision direction (step S5). The MIP image creating unit 12 then determines whether or not the newly set voxel of interest is inside the range of the volume data 23 (step S6). When the MIP image creating unit 12 determines at step S6 that the newly set voxel of interest is inside the range of the volume data 23, it compares the luminance value of the zeroth voxel that is stored and the luminance value of the newly set first voxel (step S7). At step S7, when the luminance value of the first voxel that is the voxel of interest is greater than the luminance value of the zeroth voxel, the MIP image creating unit 12 stores the luminance value of the voxel of interest as the maximum luminance value (step S8). The MIP image creating unit 12 takes the Z coordinate of the voxel of interest having the thus-stored maximum luminance value as being, for example, 1, and stores this value together with the newly determined maximum luminance value (step S9). The MIP image creating unit 12 then moves the voxel of interest towards the rear side by the amount of one voxel from the first voxel in the line of vision direction (step S10). At step S7, when the luminance value of the first voxel that is the voxel of interest is less than or equal to the luminance value of the zeroth voxel, the MIP image creating unit 12 proceeds to step S10 to move the voxel of interest towards the rear side by the amount of one voxel from the first voxel in the line of vision direction.

After step S10, the MIP image creating unit 12 repeats the steps from step S6 to step S10. When the MIP image creating unit 12 determines at step S6 that the voxel of interest is outside the range of the volume data 23, the MIP image creating unit 12 proceeds to step S1. After the MIP image creating unit 12 performs the calculations of step S2 to step S10 for all pixels on the plane of projection and completes the calculations at each pixel on the plane of projection, it displays the calculated MIP image on the plane of projection (step S11).

The MIP image that is calculated as described above will now be described using FIGS. 5A and 5B.

Figure 5A:
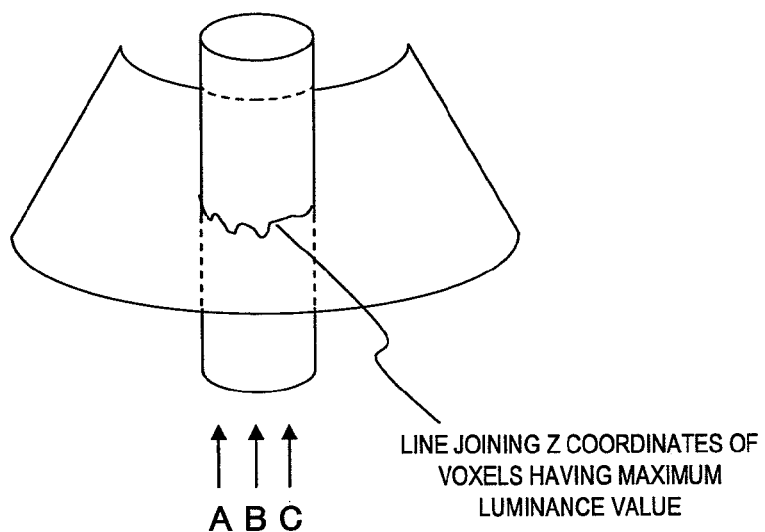
FIGS. 5A and 5B are views for describing an example of luminance value processing in the MIP method.
Figure 5B:
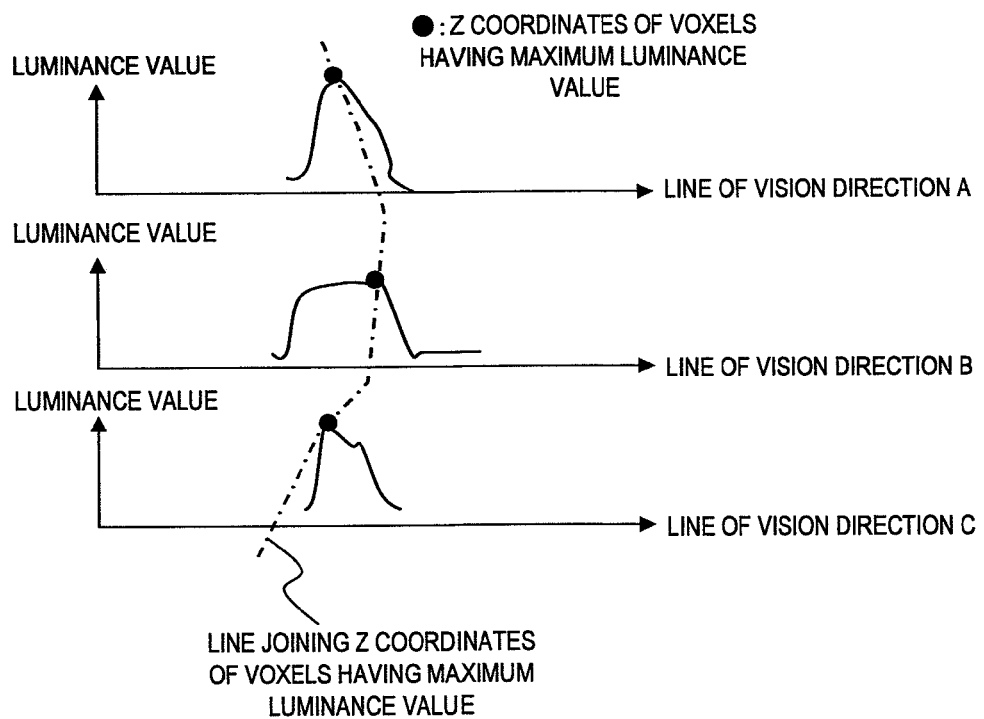

FIG. 5B schematically shows examples of graphs representing changes in a luminance value for a direction of a line of vision A, a direction of a line of vision B, and a direction of a line of vision C, respectively, that are schematically shown in FIG. 5A. In each of the graphs shown in FIG. 5B, the axis of abscissa represents the Z coordinate of a voxel in each line of vision direction and the axis of ordinate represents the luminance value of a voxel at each Z coordinate. When determining the Z coordinates of voxels having the maximum luminance value in each line of vision direction, as described in FIG. 4, in some cases a line joining the Z coordinates of the voxels having the maximum luminance value in each line of vision direction forms a line that bends back and forth little by little and is difficult to recognize, as shown in FIGS. 5A and 5B.

Figure 6:
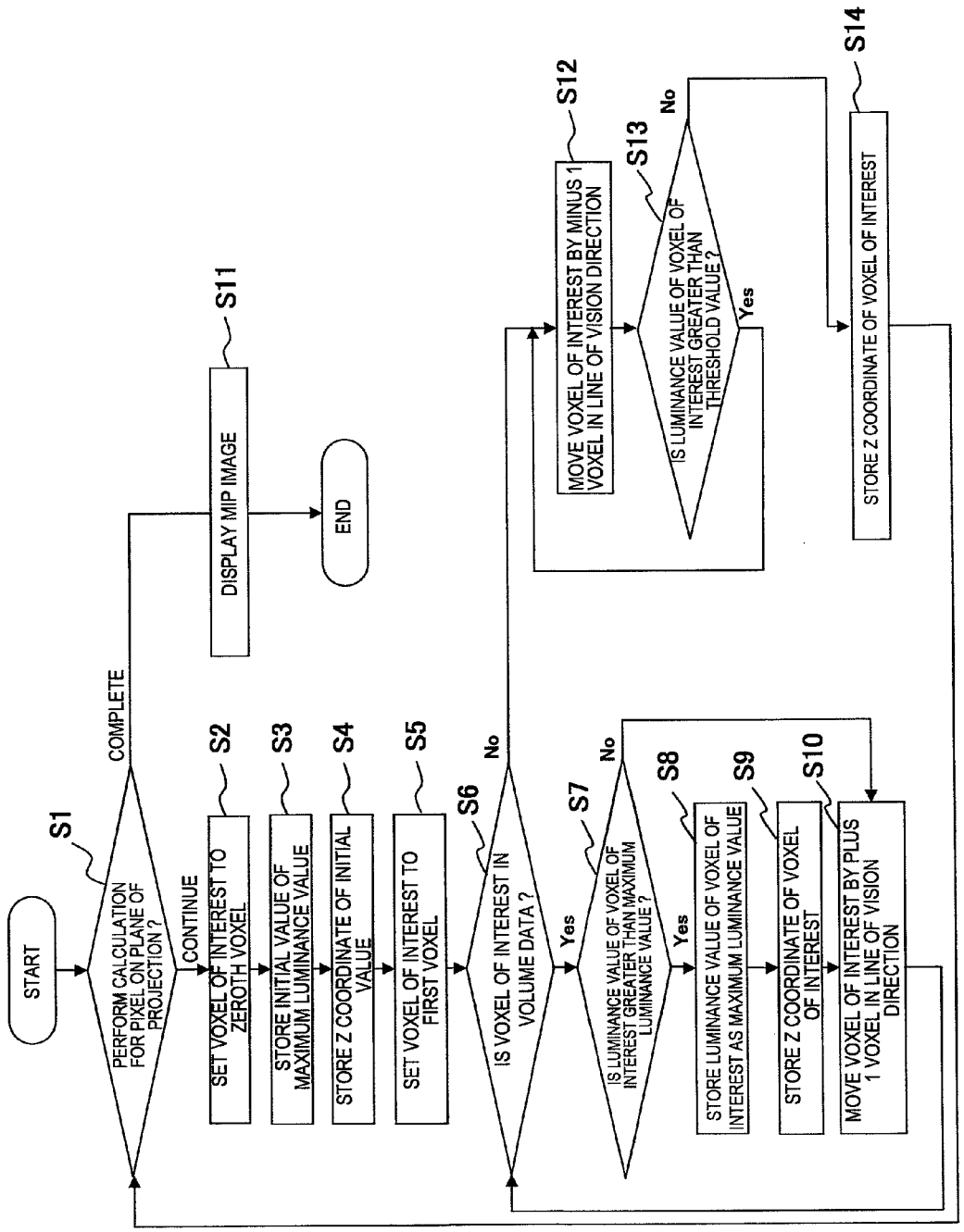
FIG. 6 is a view that illustrates other operation procedures of the MIP method.

Therefore, according to another example of the operation procedures of the MIP image creating unit 12 shown in FIG. 6, the luminance values are processed using a threshold value. In FIG. 6, sections that are the same as sections described for FIG. 4 are assigned the same reference numerals, and a description of those sections is omitted.

In FIG. 6, when the MIP image creating unit 12 determines at step S6 that the voxel of interest is outside the range of the volume data 23, it moves the voxel of interest by the amount of minus one (−1) voxel in the line of vision direction (that is, the voxel of interest is returned by the amount of one voxel toward the front side in the line of vision direction) (step S12). The MIP image creating unit 12 then compares the luminance value of the voxel of interest with a preset threshold value (step 13). At step S13, when the luminance value of the voxel of interest is greater than the preset threshold value, the MIP image creating unit 12 returns to step S112 to move the voxel of interest by a further amount of minus one (−1) voxel in the line of vision direction. At step S13, when the luminance value of the voxel of interest is less than or equal to the preset threshold value, the MIP image creating unit 12 regards the Z coordinate of the voxel having the luminance value for the threshold value as the Z coordinate of a voxel having the maximum luminance value, and stores that Z coordinate (step S14). The MIP image creating unit 12 then proceeds to step S1.

Figure 7A:
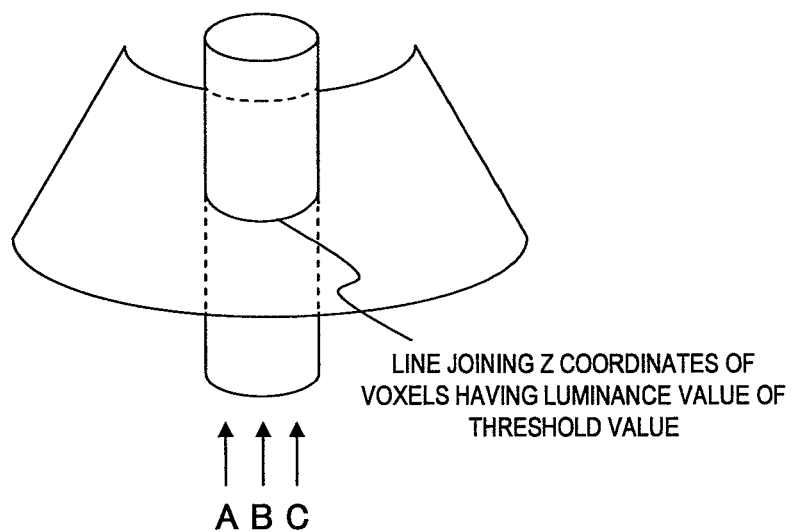
FIGS. 7A and 7B are views for describing another example of luminance value processing in the MIP method.
Figure 7B:
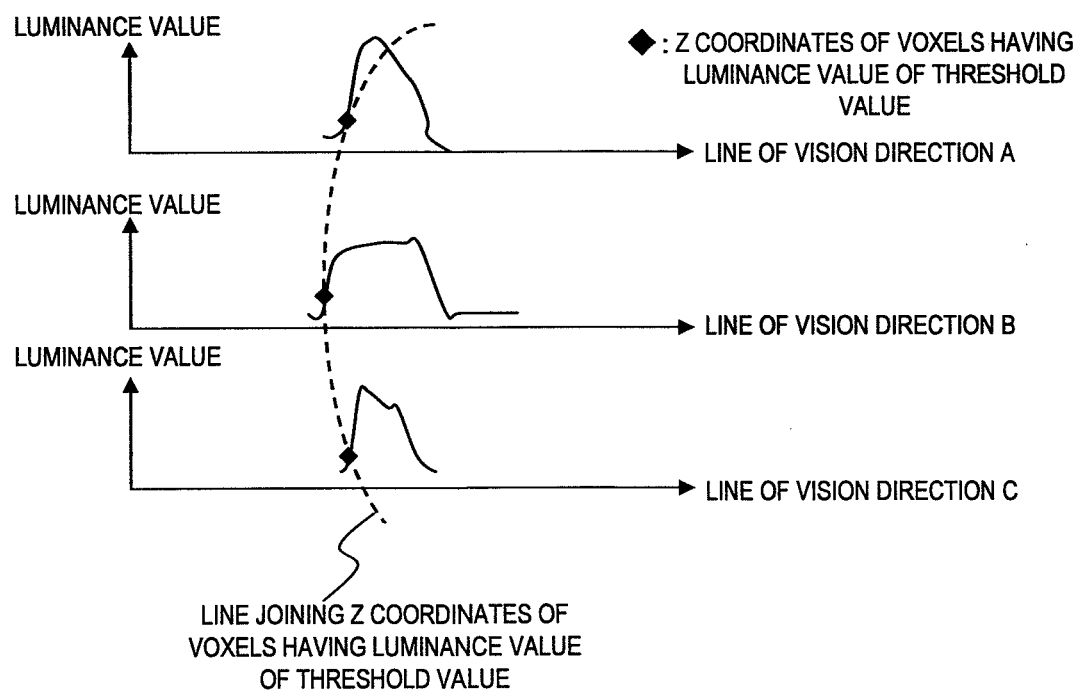

In a case in which the MIP image creating unit 12 performs the operations shown in FIG. 6 for a case in which the luminance value changes are the same as those shown in FIGS. 5A and 5B, as shown in FIGS. 7A and 7B, since a line joining the Z coordinates of voxels having a luminance value of the threshold value in each line of vision direction is smoother than the line joining the Z coordinates of voxels having the maximum luminance value shown in FIGS. 5A and 5B, the display of the MIP image is easy to recognize.

In this case, a threshold value for the luminance value may be set automatically by a program or may be input manually by an operator. When setting the threshold value with a program, it is sufficient to use as a threshold value a value that is obtained by multiplying the maximum luminance value stored at step S8 by a constant less than 1.

Further, as the decision conditions at step S13, the condition "gradient of luminance values at voxels of interest (i.e. gradient of each graph shown in FIG. 7B) is less than or equal to a certain threshold value" may be used in place of "luminance value of voxel of interest is greater than preset threshold value". In this case, the gradient of the luminance values is calculated using the proximal three voxels or proximal nine voxels with respect to the voxel of interest. The term "proximal three voxels" refers to a voxel positioned the amount of minus one (−1) voxel from the voxel of interest in the line of vision direction (Z direction), a voxel positioned the amount of plus one (+1) voxel from the voxel of interest in the line of vision direction, and the voxel of interest itself. The term "proximal nine voxels" refers to nine voxels that are in the range of plus/minus one (+/−1) voxel in the X direction, Y direction, and Z direction (line of vision direction) taking the voxel of interest as the center.

Figure 8:
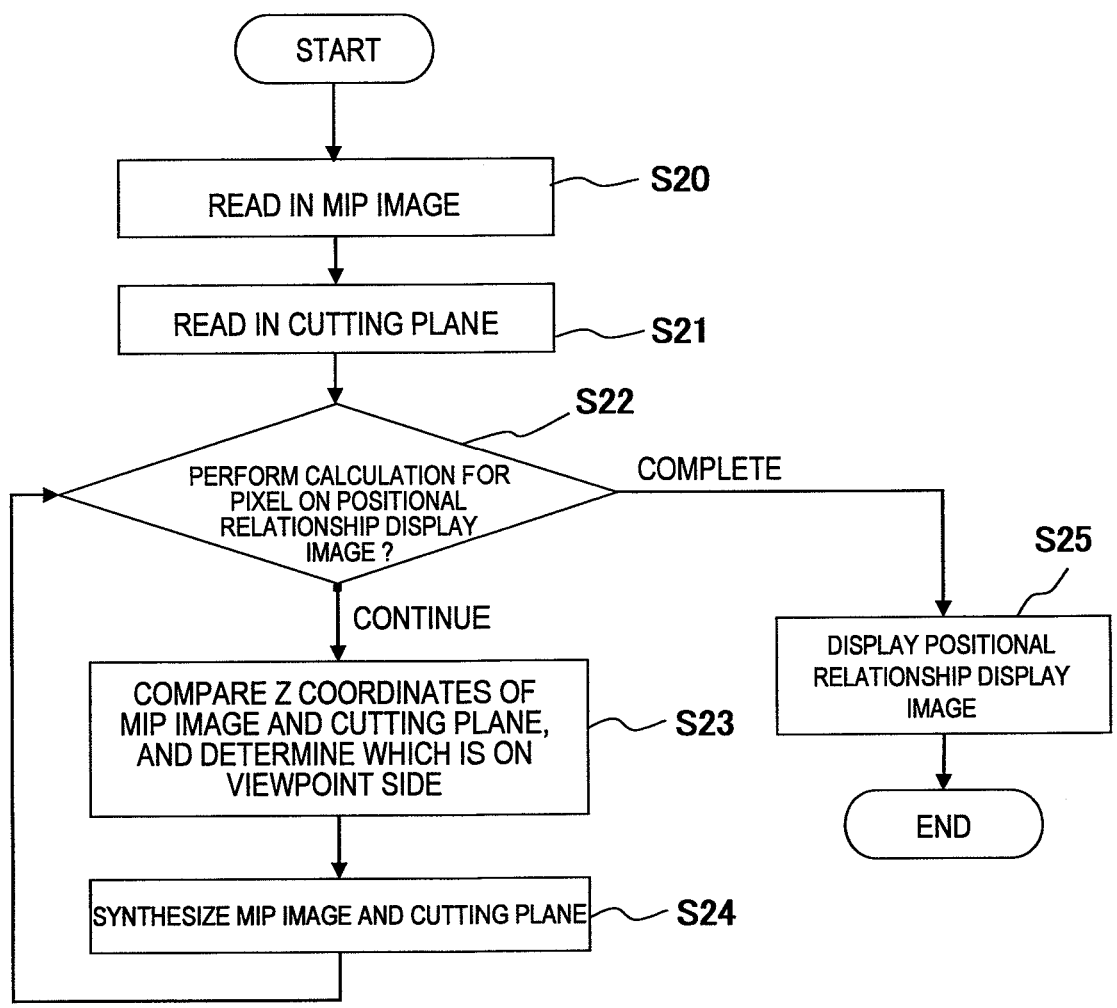
FIG. 8 is a view that illustrates operation procedures that create a positional relationship display image.

Next, the operation procedures of the positional relationship display image creating unit 14 are described using FIG. 8.

First, the positional relationship display image creating unit 14 reads in an MIP image that is created by the MIP image creating unit 12 (step S20). The positional relationship display image creating unit 14 then reads in a cutting plane created by the cutting plane creating unit 13 on the three-dimensional space of the MIP image (step S21). Next, the positional relationship display image creating unit 14 determines whether or not to perform an image creating calculation based on the mutual positional relationship between the cutting plane and the MIP image with respect to pixels on the positional relationship display image (step S22). The positional relationship display image creating unit 14 then determines whether the MIP image or the cutting plane is nearer to the viewpoint 21 by comparing the Z coordinate value of a voxel having the maximum luminance value on the line of vision 22 of the MIP image and the Z coordinate value of the cutting plane at the plane of projection of the cutting plane created by the cutting plane creating unit 13 (step S23). Next, the positional relationship display image creating unit 14 performs translucent synthesis in sequence from the image that is determined to be closer to the viewpoint 21 among the MIP image and the cutting plane. In this case, the opacity of the MIP image and the cutting plane, respectively, are preset, and the luminance is added at a ratio in accordance with their opacities (step S24).

More specifically, when the MIP image is closer to the viewpoint 21 than the cutting plane, at step S24 the luminance of the positional relationship display image is calculated by the following formula (3):
[Formula 3]

$$L_P = L_M \times O_M + (1-O_M) \times L_S \times O_S \qquad (3)$$

Here, $L_P$ represents the luminance of the positional relationship display image, $L_M$ represents the luminance of the MIP image, $L_S$ represents the luminance of the cutting plane, $O_M$ represents the opacity of the MIP image, $O_S$ represents the opacity of the cutting plane, and $(1-O_M)$ corresponds to the transparency of the MIP image.

In contrast, when the cutting plane is closer to the viewpoint 21 than the MIP image, at step S24 the luminance of the positional relationship display image is calculated by the following formula (4):
[Formula 4]

$$L_P = L_S \times O_S + (1-O_S) \times L_M \times O_M \qquad (4)$$

Here, $(1-O_S)$ corresponds to the transparency of the cutting plane.

Next, if the positional relationship display image creating unit 14 determines at step S22 that an image creating calculation based on the mutual positional relationship between the MIP image and the cutting plane is completed for all pixels on the positional relationship display image, it displays the calculated positional relationship display image on the display unit 15 (step S25).

As described above, according to the first embodiment of the present invention, by creating and displaying a positional relationship display image based on the mutual positional relationship between an MIP image and a cutting plane, the mutual positional relationship between the MIP image and the cutting plane can be clearly recognized by an operator.

Figure 9:
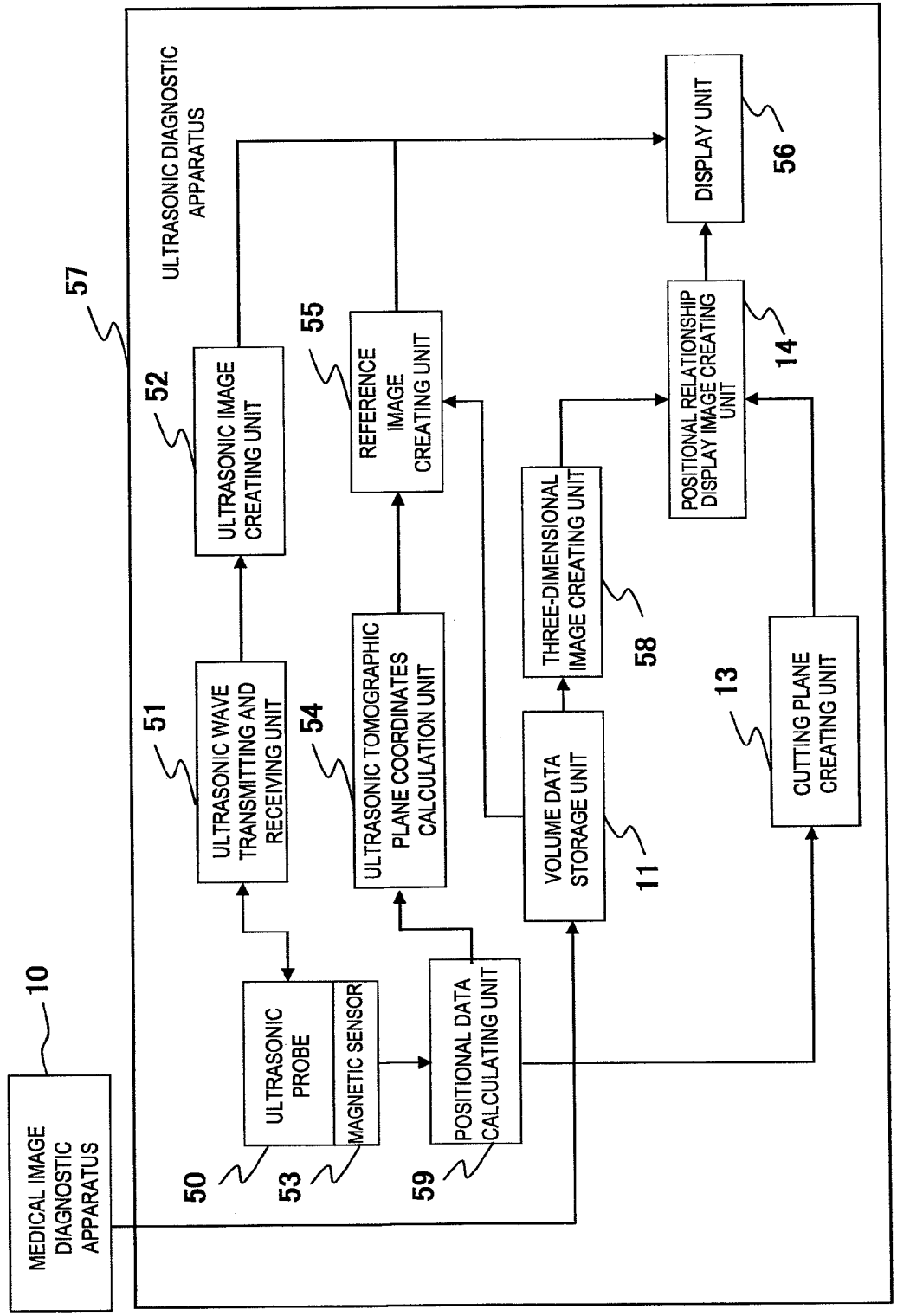
FIG. 9 is a configuration diagram that illustrates a second embodiment of the present invention.
Figure 10:
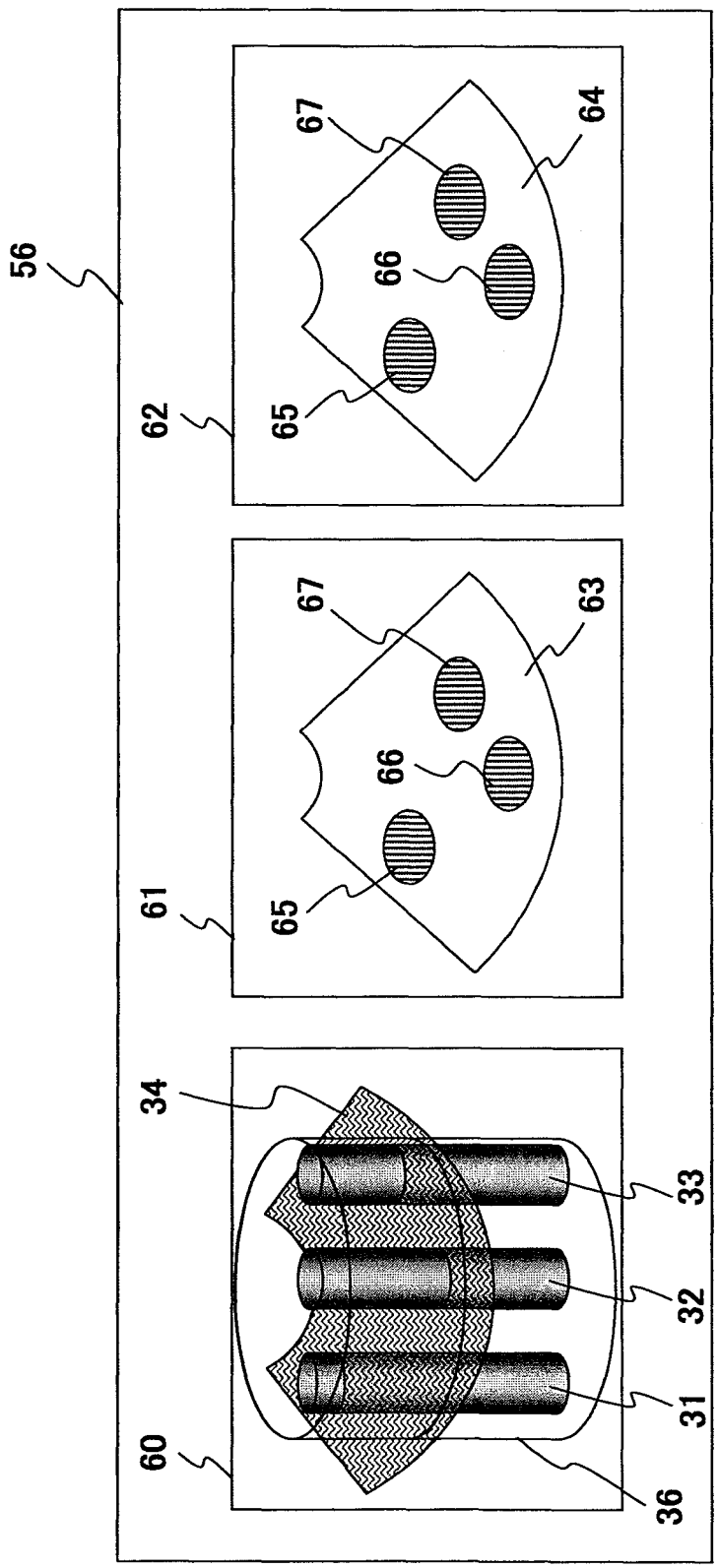
FIG. 10 is a view for describing a display mode of the second embodiment.

Next, the second embodiment of the present invention is described using FIGS. 9 and 10. The second embodiment differs from the first embodiment in that, in addition to a body surface image of an object to be examined as a display image, a positional relationship display image is created and displayed so as to represent the mutual positional relationship between an MIP image, a cutting plane, and the body surface image. A positional relationship display image to which a body surface image is added can be used as a guide image for real-time virtual sonography (RVS). RVS refers to technology that, when picking up ultrasonic images of an object to be examined with an ultrasonic diagnostic apparatus, extracts a reference image (for example, a CT tomogram) matching a display cross section of an ultrasonic image being imaged from three-dimensional volume data relating to the object that is previously acquired by various medical image diagnostic apparatuses (for example, a CT image diagnostic apparatus), and displays the extracted reference image on the display screen in parallel with the ultrasonic image being imaged. As a result, at the ultrasonic diagnostic apparatus, it is possible to render in real time a reference image of the same cross section as the ultrasonic image being imaged.

FIG. 9 is a system configuration diagram of a medical image diagnostic system according to the second embodiment. An ultrasonic diagnostic apparatus 57 includes an ultrasonic probe (hereunder, referred to as "probe") 50 that transmits and receives ultrasonic waves to and from an object to be examined, an ultrasonic wave transmitting and receiving unit 51 that supplies a driving signal to the probe 50 and processes a reception signal output from the probe 50 to output reception data, an ultrasonic image creating unit 52 that reconstructs an ultrasonic image based on reception data output from the ultrasonic wave transmitting and receiving unit 51, and a display unit 56 that displays an ultrasonic image output from the ultrasonic image creating unit 52.

The ultrasonic diagnostic apparatus 57 further comprises a volume data storage unit 11 that takes in and stores volume data relating to an object to be examined that is acquired by the medical image diagnostic apparatus 10.

In the probe 50, a plurality of diagnostic transducers are arrayed that transform driving signals into ultrasonic waves to deliver the waves to a target site of an object to be examined, and also capture a reflected echo that is generated from the target site of the object and transform the echo into a reception signal. In addition to the diagnostic transducers, a plurality of therapeutic transducers that deliver therapeutic ultrasonic waves to the target site of the object may also be arrayed in the probe 50.

The ultrasonic diagnostic apparatus 57 comprises a magnetic position sensor system. The magnetic position sensor system has a magnetic field generator (not shown) that is attached to a bed or the like on which an object to be examined lies, a magnetic signal detector (magnetic sensor) 53 that is attached to the probe 50, and a positional data calculating unit 59 that calculates data (hereunder, referred to as "positional data") representing the three-dimensional position or inclination (twisting) or the like of the probe 50 based on detection signals output from the magnetic sensor 53, and outputs the data to an ultrasonic tomographic plane coordinates calculation unit 54 and the cutting plane creating unit 13.

The ultrasonic tomographic plane coordinates calculation unit 54 acquires positional data of the probe 50 and outputs the data to a reference image configuration unit 55. At a time of real-time imaging, the reference image configuration unit 55 acquires positional data corresponding to an ultrasonic image that is currently being imaged in real time from the ultrasonic tomographic plane coordinates calculation unit 54.

The volume data storage unit 11 stores volume data acquired from the medical image diagnostic apparatus 10 in a memory or the like together with the three-dimensional position coordinates thereof. The volume data storage unit 11 can also store a plurality of kinds of volume data acquired by various image diagnostic apparatuses.

The reference image configuration unit 55 extracts reference image data from volume data stored in the volume data storage unit 11 based on positional data of the probe 50 that is output from the ultrasonic tomographic plane coordinates calculation unit 54, and configures a reference image. At a time of real-time imaging, this reference image data corresponds to a scanning surface of the ultrasonic image currently being imaged. The reference image is displayed on the display unit 56 as a tomogram of the same cross section as the ultrasonic image being imaged.

The ultrasonic diagnostic apparatus 57 comprises, as a device which creates guide information of the probe 50, a three-dimensional image creating unit 58 that creates an MIP image and a surface rendering (SR) image based on volume data stored in the volume data storage unit 11 and synthesizes these, a cutting plane creating unit 13 that creates a cutting plane of a three-dimensional space, and a positional relationship display image creating unit 14 that creates a positional relationship display image representing the mutual positional relationship between an MIP image and a cutting plane. The positional relationship display image created with the positional relationship display image creating unit 14 serves as guide information of the probe 50, and the operator moves the probe 50 based on that guide information. The ultrasonic diagnostic apparatus 57 comprises a control unit that controls each component and an operation unit (not shown).

The method of creating guide information will now be described in detail. The three-dimensional image creating unit 58 creates an MIP image using the MIP method described in the first embodiment based on volume data stored in the volume data storage unit 11, and also creates an image (in this case, referred to as an "SR image") that represents the body surface of an object to be examined using a surface rendering (SR) method or a volume rendering (VR) method based on volume data stored in the volume data storage unit 11.

According to the surface rendering method, a viewpoint and a plane of projection are set by the operator with respect to volume data, the surface boundary of an object to be examined is extracted by threshold value processing or the like from the volume data, and as the projection values for each pixel (coordinates (X, Y)) on the plane of projection, results obtained by shading processing based on an angle formed by a line of vision vector and a normal line vector of the boundary surface are reflected in projection values. At this time, the Z coordinate of the surface boundary is employed for the depth information (Z coordinate).

According to the volume rendering method, a viewpoint and a plane of projection are set by the operator with respect to volume data, and as projection values with respect to each pixel (coordinates (X, Y)) on the plane of projection, the luminance of a voxel on the line of vision is added while being weighted according to the opacity of each pixel. At this time, the Z coordinate of a place at which the luminance value is greater than a certain threshold value or the Z coordinate of a place at which the luminance gradient is greater than a certain threshold value is employed for the depth information (Z coordinate).

When creating a three-dimensional image for which an image of a blood vessel section is created with the MIP method and an image of a body surface of an object to be examined is created with the surface rendering method or the volume rendering method, the three-dimensional image creating unit 58 collectively calculates the depth information (Z coordinates) of the MIP image and the SR image in the three-dimensional space.

The three-dimensional image creating unit 58 synthesizes the MIP image and SR image created as described above. When synthesizing the MIP image and the SR image, by comparing the Z coordinate of the MIP image and the Z coordinate of the SR image; the three-dimensional image creating unit 58 executes hidden surface removal processing with respect to the image among the MIP image and the SR image that is farther from the viewpoint 21 and is in the shadow of the other image and cannot be seen. Normally, an image of blood vessels (MIP image) is disposed further on the rear side than an image of the body surface (SR image). At this time, the respective opacities are set for the MIP image and the SR image, and by blending the luminance value of the MIP image and the luminance value of the SR image at a ratio that corresponds to the Z coordinate values and a coefficient corresponding to the opacities, the SR image on the front side is displayed translucently and the MIP image on the rear side is displayed through the SR image. Since this synthesized three-dimensional image represents the positional relationship between the blood vessels and body surface of an object to be examined, the operator can clearly recognize which blood vessels inside the object are being displayed and in which direction from which position the blood vessels are being observed.

The cutting plane creating unit 13 creates a cutting plane inside a three-dimensional space based on positional data (three-dimensional position and inclination (twisting) of the probe 50) of the magnetic sensor 53 that is output from the positional data calculating unit 59. More specifically, the cutting plane creating unit 13 moves the three-dimensional position of the cutting plane in accordance with the three-dimensional position of the probe 50 by changing ($X_0, Y_0, Z_0$) in the plane formula (Formula (2)) described in the embodiment based on the three-dimensional position of the probe 50. Further, the cutting plane creating unit 13 rotates the cutting plane in a manner taking a normal line of the cutting plane that passes through the center of the cutting plane as an axis in accordance with rotation of the probe 50 by changing the rotational component R (Formula (1)) described in the first embodiment based on the inclination (twisting) of the probe 50 and rotating the cutting plane taking the center of the cutting plane as a pivoting point.

The positional relationship display image creating unit 14 creates a positional relationship display image that represents the mutual positional relationship between a three-dimensional image in which an SR image and an MIP image created by the three-dimensional image creating unit 58 are synthesized and a cutting plane created by the cutting plane creating unit 13.

With regard to the relationship between the MIP image, the SR image, and the cutting plane, similarly to the description in the first embodiment, the respective Z coordinate values are compared for the MIP image, the SR image, and the cutting plane and rearranged in the order of images closest to the viewpoint 21 (rearrangement in Z order), and then subjected to hidden surface removal processing. The nearer an image is to the viewpoint 21, the further on the front side the image in question is displayed.

In this case, the method of creating a positional relationship display image involves setting the opacity for the MIP image, the SR image, and the cutting plane, respectively, and then performing a process of weighted addition on luminance values in the Z order in a manner whereby the higher the level of opacity that is set, the greater the weighting that is applied to the coefficient. More specifically, for example, in a case in which, at a certain position (XY) on the plane of projection, the cutting plane, the SR image, and the MIP image are aligned in that order from the viewpoint 21, and the opacity of the cutting plane and the SR image is set low and the opacity of the MIP image is set high, in the positional relationship display image the SR image and the cutting plane on the front side from the viewpoint are displayed translucently and the MIP image that is on the rear side thereof is displayed through the cutting plane and the SR image. Further, when the Z coordinate value of the MIP image and the Z coordinate value of the cutting plane are equal, a luminance value at the position (XY) on the positional relationship display image is set to be represented in, for example, blue. Also, when the Z coordinate value of the SR image and the Z coordinate value of the cutting plane are equal, a luminance value at the position (XY) on the positional relationship display image is set to be represented in, for example, yellow. Thus, in the positional relationship display image, a boundary line between the cutting plane and the MIP image is represented in blue and a boundary line between the cutting plane and the SR image is represented in yellow. Consequently, the boundary lines are clear.

As shown in FIG. 10, the display unit 56 displays a positional relationship display image 60 created by the positional relationship display image creating unit 14, an ultrasonic image 63 created by the ultrasonic image creating unit 52, and a reference image 64 created by the reference image configuration unit 55.

In the positional relationship display image 60, since the cutting plane 34 is displayed together with an image of blood vessels 31, 32, and 33 displayed as an MIP image, the operator can recognize from the positional relationship between the respective blood vessels 31, 32, and 33 and the cutting plane 34 that the blood vessel 32 is located furthest on the front side, the blood vessel 31 is located furthest on the rear side, and the blood vessel 33 is located between the blood vessel 32 and the blood vessel 31, to thereby recognize the depth relationship between the blood vessels 31, 32, and 33. Further, in the composite image 60, since an SR image 36 representing the body surface of an object to be examined is displayed together with the image of the blood vessels 31, 32, and 33 and the cutting plane 34, the operator can recognize the three-dimensional positional relationship between the body surface of the object and the blood vessels 31, 32, and 33.

The ultrasonic image 63 and the reference image 64 are tomograms of an object to be examined that correspond to the cutting plane 34. The ultrasonic image 63 and the reference image 64 respectively display cross-sectional images 65, 66, and 67 that respectively correspond to cross sections of blood vessels 31, 32, and 33 that are cut by the cutting plane 34. Accordingly, the operator can also recognize the depth relationship of the blood vessels 31, 32, and 33 from the ultrasonic image 63 and the reference image 64.

A display screen that is displayed by the display unit 56 has a display area 61 in which an ultrasonic image 63 that is being imaged is displayed, a display area 62 in which a reference image 64 with the same display cross section as the ultrasonic image 63 is displayed, and a display area in which guide information of the composite image 60 is displayed. A configuration may also be adopted in which the display area 61 and the display area 62 are displayed side-by-side, and the display area in which the guide information of the composite image 60 is displayed is disposed below the display area 61 and the display area 62. A configuration for displaying the display areas is not limited to these display modes, and the position of the display area in which the guide information of the composite image is displayed may be changed within a range that does not hinder diagnosis. Further, it is desirable that the position of the probe 50 that is capturing the ultrasonic image is displayed in a condition in which it is superimposed on a body mark. A configuration may also be adopted that allows the operator to move the position of each display area inside the display screen via the operation unit.

Figure 11A:
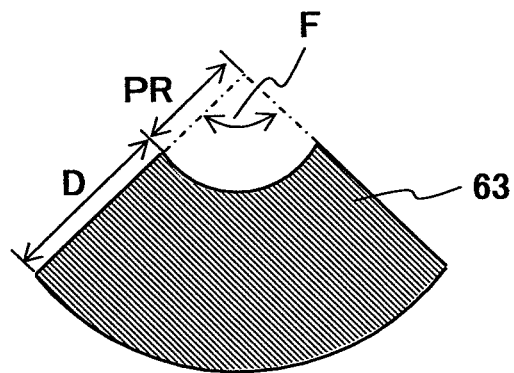
FIGS. 11A, 11B, and 11C are views for describing the shapes of ultrasonic images.
Figure 11B:
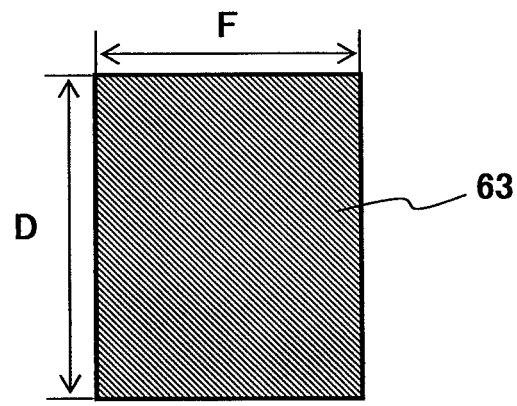
Figure 11C:
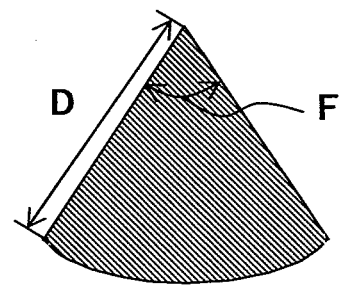

FIGS. 11A, 11B, and 11C are views that illustrate the shape of the ultrasonic image 63. The ultrasonic image 63 of the embodiment shown in FIG. 10 is obtained by the ultrasonic probe 50 that has a convex shape. As shown in FIG. 11A, a probe radius PR of the probe 50 as well as the depth D and field of view F of the ultrasonic image 63 are shown in accordance with the shape of the ultrasonic image 63. In the embodiment shown in FIG. 10, the shape of the cutting plane 34 and the reference image 64 is assumed to be a convex shape, which matches the shape of the ultrasonic image 63.

FIG. 11B is a view that describes an ultrasonic image 63 obtained by a linear-shaped ultrasonic probe 50. FIG. 11C is a view that describes an ultrasonic image 63 obtained by a sector-shaped ultrasonic probe 50. In each of these figures, the field of view F and depth D of the ultrasonic image 63 is represented in accordance with the shape of the ultrasonic image 63. The ultrasonic probe may also be in the shape of a three-dimensional scan. It is desirable that the shape of the cutting plane 34 and the reference image 64 is determined in accordance with the shapes of these ultrasonic images 63.

Although an MIP image is described as an example of a three-dimensional image in the above embodiments, apart from an MIP image, a three-dimensional image produced by volume rendering or a MinIP (Minimum Intensity Projection) image may also be applied. MinIP processing is processing that extracts minimum values for respective voxels on the line of vision 22 to obtain a projection image.

Although when synthesizing an MIP image or an SR image and a cutting plane according to the above embodiments, the depth is represented by adjusting and combining the luminance of the respective pixels, i.e. the opacity of the images, a configuration may be adopted in which the hue of pixels or another image element is adjusted.

Further, although according to the above embodiments the magnetic sensor 53 is used for obtaining three-dimensional positional information of the ultrasonic probe 50, a sensor that obtains three-dimensional positional information by infrared rays or ultrasonic waves or the like may also be used.

Industrial Applicability

According to the above described image display method and medical image diagnostic system, a three-dimensional image to which depth information is assigned can be created and displayed.

The invention claimed is:

1. An image display method, comprising:
a three-dimensional image creating step of creating a three-dimensional image based on volume data by a maximum intensity projection of the volume data from a viewpoint to a projection plane, wherein for each of pixels forming the three-dimensional image, a maximum intensity voxel having a maximum intensity among a string of the volume data on a line of vision that passes through the volume data from the viewpoint and reaches the pixel on the projection plane is determined, and an intensity and a Z coordinate on a Z axis along the line of view, of the maximum intensity voxel are taken respectively as an intensity and a Z coordinate of the pixel;
a cutting plane setting step of setting a cutting plane which cuts the three-dimensional image at an arbitrary position; and
a positional relationship display image creating step of creating a positional relationship display image which represents a mutual positional relationship between the three-dimensional image and the cutting plane, wherein in the positional relationship display image, an opacity of a first portion of the cutting plane is adjusted so that a first portion of the three-dimensional image that is hidden by the first portion of the cutting plane is visually recognizable through the first portion of the cutting plane while the first portion of the cutting plane is visually recognizable over the first portion of the three-dimensional image in the positional relationship display image, and an opacity of a second portion of the three-dimensional image is adjusted so that a second portion of the cutting plane that is hidden by the second portion of the three-dimensional image is visually recognizable through the second portion of the three-dimensional image while the second portion of the three-dimensional image is visually recognizable over the second portion of the cutting plane in the positional relationship display image,
wherein in the positional relationship display image creating step,
the mutual positional relationship between the three-dimensional image and the cutting plane in relation to the viewpoint is determined in accordance with the Z coordinate of each of the pixels forming the three-dimensional image and a Z coordinate on the Z axis of the cutting plane, when the three-dimensional image is closer to the viewpoint than the cutting plane, an intensity of the positional relationship display image is calculated as a combination of an intensity of the three-dimensional image and an opacity of the three-dimensional image added to a combination of a transparency of the three-dimensional image, an intensity of the cutting plane and an opacity of the cutting plane, and when the cutting plane is closer to the viewpoint than the three-dimensional image, the intensity of the positional relationship display image is calculated as a combination of the intensity of the cutting plane, the opacity of the cutting plane added to a combination of a transparency of the cutting plane, the intensity of the three-dimensional image and the opacity of the three-dimensional image.

2. The image display method according to claim 1, wherein in the positional relationship display image creating step, the opacity in the positional relationship display image of at least one of the three-dimensional image and the cutting plane is adjusted so that a portion in which the three-dimensional image and the cutting plane overlap and a portion in which the three-dimensional image and the cutting plane do not overlap are displayed differently in the positional relationship display image.

3. The image display method according to claim 1, wherein in the positional relationship display image creating step, the opacity in the positional relationship display image of at least one of the three-dimensional image and the cutting plane is adjusted so that, in at least one portion of two portions into which the three-dimensional image is divided by the cutting plane, a portion in which the three-dimensional image and the cutting plane overlap and a portion in which the three-dimensional image and the cutting plane do not overlap are displayed differently in the positional relationship display image.

4. The image display method according to claim 1, wherein in the positional relationship display image creating step, the opacity in the positional relationship display image of at least one of the three-dimensional image and the cutting plane is adjusted so that a portion in which the three-dimensional image and the cutting plane do not overlap, a portion in which the three-dimensional image and the cutting plane overlap in one portion of two portions into which the three-dimensional image is divided by the cutting plane, and a portion in which the three-dimensional image and the cutting plane overlap in another portion of the two portions into which the three-dimensional image is divided by the cutting plane are displayed differently in the positional relationship display image.

5. The image display method according to claim 4, wherein in the positional relationship display image creating step, a reference point is set and the opacity in the positional relationship display image of the at least one of the three-dimensional image and the cutting plane is adjusted based on a mutual positional relationship between the reference point, the three-dimensional image, and the cutting plane.

6. The image display method according to claim 5, wherein in the positional relationship display image creating step, the opacity in the positional relationship display image of the at least one of the three-dimensional image and the cutting plane is adjusted so that one of the three-dimensional image and the cutting plane that is closer to the reference point is more distinctly recognizable visually.

7. The image display method according to claim 5, wherein in the positional relationship display image creating step, the opacity in the positional relationship display image of the at least one of the three-dimensional image and the cutting plane is adjusted so that one of the three-dimensional image and the cutting plane that is farther from the reference point is less distinctly recognizable visually.

8. The image display method according to claim 1, further comprising a body surface image creating step that creates a body surface image of a subject based on the volume data, wherein in the positional relationship display image creating step, the positional relationship display image is created so as to represent a mutual positional relationship between the three-dimensional image, the cutting plane, and the body surface image.

9. The image display method according to claim 8, wherein in the positional relationship display image creating step, the opacity in the positional relationship display image of at least one of the three-dimensional image, the cutting plane, and the body surface image is adjusted so that a portion of the three-dimensional image that is hidden by at least one of the body surface image and the cutting plane is visually recognizable through the at least one of the body surface image and the cutting plane in the positional relationship display image.

10. The image display method according to claim 8, wherein in the positional relationship display image creating step, the positional relationship display image is created so that a color of a boundary line between the cutting plane and the body surface image and a color of a boundary line between the cutting plane and the three-dimensional image are different.

11. The image display method according to claim 1, wherein in the three-dimensional image creating step, the three-dimensional image is created as a three-dimensional image that represents an external shape of tissue including the maximum intensity voxel having the maximum intensity that is obtained by the maximum intensity projection.

12. The image display method according to claim 11, wherein in the three-dimensional image creating step, a reference point is set, and a position of a nearest voxel that is spatially nearest to the maximum intensity voxel among candidate voxels is taken to be the external shape of the tissue, wherein each of the candidate voxels has an intensity equal to or less than a predetermined threshold value and is spatially positioned between the maximum intensity voxel and the reference point.

13. The image display method according to claim 11, wherein in the three-dimensional image creating step, a reference point is set, and a position of a nearest voxel that is spatially nearest to the maximum intensity voxel among candidate voxels is taken to be the external shape of the tissue, wherein each of the candidate voxels has an intensity gradient equal to or less than a predetermined threshold value and is spatially positioned between the maximum intensity voxel and the reference point.

14. The image display method according to claim 1, wherein in the positional relationship display image creating step, by setting the opacity of the three-dimensional image and the opacity of the cutting plane and performing a process of weighted addition on the three-dimensional image and the cutting plane using coefficients that are in accordance with the respective opacities thereof, the positional relationship display image is created as an image in which at least one of the three-dimensional image and the cutting plane is made translucent.

15. The image display method according to claim 1, wherein in the positional relationship display image creating step, when the three-dimensional image is closer to the viewpoint than the cutting plane, the intensity of the positional relationship display image is calculated by the following formula:

$$L_P = L_M \times O_M + (1-O_M) \times L_S \times O_S, \text{ and}$$

when the cutting plane is closer to the viewpoint than the three-dimensional image, the intensity of the positional relationship display image is calculated by the following formula:

$$L_P = L_S \times O_S + (1-O_S) \times L_M \times O_M,$$

where $L_P$ represents the intensity of the positional relationship display image, $L_M$ represents the intensity of the three-dimensional image, $L_S$ represents the intensity of the cutting plane, $O_M$ represents the opacity of the three-dimensional image, $O_S$ represents the opacity of the cutting plane, $(1-O_M)$ corresponds to the transparency of the three-dimensional image, and $(1-O_S)$ corresponds to the transparency of the cutting plane.

16. A medical image diagnostic system, comprising:

a volume data storage device which stores volume data relating to a subject;

a three-dimensional image creating device which creates a three-dimensional image based on the volume data by a maximum intensity projection of the volume data from a viewpoint to a projection plane, wherein for each of pixels forming the three-dimensional image, the three-dimensional image creating device determines a maximum intensity voxel having a maximum intensity among a string of the volume data on a line of vision that passes through the volume data from the viewpoint and reaches the pixel on the protection plane, and the three-dimensional image creating device takes an intensity and a Z coordinate on a Z axis along the line of view, of the maximum intensity voxel respectively as an intensity and a Z coordinate of the pixel;

a cutting plane setting device which sets a cutting plane that cuts the three-dimensional image at an arbitrary position; and a positional relationship display image creating device which creates a positional relationship display image which represents a mutual positional relationship between the three-dimensional image and the cutting plane, wherein in the positional relationship display image, an opacity of a first portion of the cutting plane is adjusted so that a first portion of the three-dimensional image that is hidden by the first portion of the cutting plane is visually recognizable through the first portion of the cutting plane while the first portion of the cutting plane is visually recognizable over the first portion of the three-dimensional image in the positional relationship display image, and an opacity of a second portion of the three-dimensional image is adjusted so that a second portion of the cutting plane that is hidden by the second portion of the three-dimensional image is visually recognizable through the second portion of the three-dimensional image while the second portion of the three-dimensional image is visually recognizable over the second portion of the cutting plane in the positional relationship display image, wherein the positional relationship display image creating device creates the positional relationship display image while determining the mutual positional relationship between the three-dimensional image and the cutting plane in relation to the viewpoint in accordance with the Z coordinate of each of the pixels forming the three-dimensional image and a Z coordinate on the Z axis of the cutting plane, when the three-dimensional image is closer to the viewpoint than the cutting plane, the positional relationship display image creating device calculates an intensity of the positional relationship display image as a combination of an intensity of the three-dimensional image and an opacity of the three-dimensional image added to a combination of a transparency of the three-dimensional image, an intensity of the cutting plane and an opacity of the cutting plane, and when the cutting plane is closer to the viewpoint than the three-dimensional image, the positional relationship display image creating device calculates the intensity of the positional relationship display image as a combination of the intensity of the cutting plane, the opacity of the cutting plane added to a combination of a transparency of the cutting plane, the intensity of the three-dimensional image and the opacity of the three-dimensional image.

17. The medical image diagnostic system according to claim 16, further comprising:

a probe which transmits and receives ultrasonic waves to and from the subject;

an ultrasonic wave transmitting and receiving device which supplies a driving signal to the probe and also processes a reception signal that is output from the probe to output reception data;

an ultrasonic image creating device which reconstructs an ultrasonic image based on the reception data that is output from the ultrasonic wave transmitting and receiving device; and a display device which displays at least one of the positional relationship display image and the ultrasonic image.

18. The medical image diagnostic system according to claim 17, further comprising:

a positional information acquisition device which acquires positional information of the probe; and a cutting plane moving device which causes the cutting plane to be either moved or rotated, or both moved and rotated, with respect to the three-dimensional image based on the positional information of the probe that is acquired by the positional information acquisition device.

19. The medical image diagnostic system according to claim 18, further comprising:

a reference image creating device which creates a reference image of the same cross section as the ultrasonic image based on the volume data and the positional information of the probe, wherein the display device displays the reference image.

20. The medical image diagnostic system according to claim 19, wherein at least one shape among the cutting plane shape, the ultrasonic image shape, and the reference image is one of a linear shape, a convex shape, and a sector shape.

21. The medical image diagnostic system according to claim 16, wherein:

when the three-dimensional image is closer to the viewpoint than the cutting plane, the positional relationship display image creating device calculates the intensity of the positional relationship display image by the following formula:

$$L_P = L_M \times O_M + (1-O_M) \times L_S \times O_S,$$ and when the cutting plane is closer to the viewpoint than the three-dimensional image, the positional relationship display image creating device calculates the intensity of the positional relationship display image by the following formula:

$$L_P = L_S \times O_S + (1-O_S) \times L_M \times O_M,$$

where $L_P$ represents the intensity of the positional relationship display image, $L_M$ represents the intensity of the three-dimensional image, $L_S$ represents the intensity of the cutting plane, $O_M$ represents the opacity of the three-dimensional image, $O_S$ represents the opacity of the cutting plane, $(1-O_M)$ corresponds to the transparency of the three-dimensional image, and $(1-O_S)$ corresponds to the transparency of the cutting plane.

* * * * *